US011222136B2

(12) United States Patent
Fan et al.

(10) Patent No.: US 11,222,136 B2
(45) Date of Patent: Jan. 11, 2022

(54) METHOD AND SYSTEM FOR DYNAMIC SEARCHABLE SYMMETRIC ENCRYPTION WITH FORWARD PRIVACY AND DELEGATED VERIFIABILITY

(71) Applicant: Robert Bosch GmbH, Stuttgart (DE)

(72) Inventors: Xinxin Fan, Pittsburgh, PA (US); Qingji Zheng, Pittsburgh, PA (US); Lei Yang, Lawrence, KS (US)

(73) Assignee: Robert Bosch GmbH, Stuttgart (DE)

( * ) Notice: Subject to any disclaimer, the term of this patent is extended or adjusted under 35 U.S.C. 154(b) by 310 days.

(21) Appl. No.: 16/319,556

(22) PCT Filed: Jul. 25, 2017

(86) PCT No.: PCT/EP2017/068734
§ 371 (c)(1),
(2) Date: Jan. 22, 2019

(87) PCT Pub. No.: WO2018/019815
PCT Pub. Date: Feb. 1, 2018

(65) Prior Publication Data
US 2019/0278939 A1 Sep. 12, 2019

Related U.S. Application Data

(60) Provisional application No. 62/366,320, filed on Jul. 25, 2016.

(51) Int. Cl.
*G06F 21/62* (2013.01)
*G16H 10/60* (2018.01)
(Continued)

(52) U.S. Cl.
CPC ......... *G06F 21/6245* (2013.01); *G16H 10/60* (2018.01); *H04L 9/0866* (2013.01);
(Continued)

(58) Field of Classification Search
CPC ... G06F 21/6245; G16H 10/60; H04L 9/0866; H04L 9/0891; H04L 9/3242; H04L 9/3297; H04L 2209/88; H04L 2212/00
(Continued)

(56) References Cited

U.S. PATENT DOCUMENTS

2011/0258445 A1* 10/2011 Escott ............... H04L 9/085
713/168
2012/0289787 A1* 11/2012 Kurgan .............. G16H 70/20
600/300

(Continued)

OTHER PUBLICATIONS

International Search Report corresponding to PCT Application No. PCT/EP2017/068734, dated Oct. 26, 2017 (English language document) (4 pages).

(Continued)

*Primary Examiner* — Michael S McNally
(74) *Attorney, Agent, or Firm* — Maginot, Moore & Beck LLC

(57) ABSTRACT

A DSSE architecture network enables multi-user such as data owners and data users to conduct privacy-preserving search on the encrypted PHIs stored in a cloud network and verify the correctness and completeness of retrieved search results simultaneously is provided. The data owners and data users may be patients, HSPs, or combination thereof. An IoT gateway aggregates periodically collected data into a single PHI file, extract keywords, build an encrypted index, and encrypt the PHI files before the encrypted index and PHI files are transmitted to a cloud network periodically for storage thus enable the DSSE architecture network to achieve a sub-linear search efficiency and forward privacy by maintaining an increasing counter for each keyword at the IoT gateway. Since the PHI files are always transmitted and added/stored into the cloud storage over the cloud network, file deletion, file modification is eliminated. The (Continued)

cloud network therefore does not need to learn whether the newly stored PHI files contain specific keywords. Any number of HSPs such as data users provides healthcare services for the patient by searching, querying, and/or retrieving user's encrypted PHIs incrementally stored on the cloud network in a privacy and verifiable manner. The patient delegated verifiability is derived from a combination of a Bloom filter and aggregate message authentication code.

7 Claims, 2 Drawing Sheets

(51) Int. Cl.
*H04L 9/08* (2006.01)
*H04L 9/32* (2006.01)

(52) U.S. Cl.
CPC .......... *H04L 9/0891* (2013.01); *H04L 9/3242* (2013.01); *H04L 9/3297* (2013.01); *H04L 2209/88* (2013.01); *H04L 2212/00* (2013.01)

(58) Field of Classification Search
USPC .......................................................... 726/28
See application file for complete search history.

(56) References Cited

U.S. PATENT DOCUMENTS

| | | | |
|---|---|---|---|
| 2015/0156011 A1* | 6/2015 | Kamara | G06F 21/6218 713/165 |
| 2016/0140179 A1* | 5/2016 | Yuen | G06F 16/2272 707/769 |

OTHER PUBLICATIONS

Reza Curtmola, et al., Searchable Symmetric Encryption: Improved Definitions and Efficient Constructions, International Association for Cryptologic Research, vol. 20110420:005403, Apr. 20, 2011, pp. 1-33.

Yue Tong et al., Cloud-Assisted Mobile-Access of Health Data with Privacy and Auditability, IEEE Journal of Biomedical and Health Informatics, vol. 18, No. 2, Mar. 1, 2014, pp. 419-429.

Lei Yang et al., RSPP: A Reliable, Searchable and Privacy-Preserving e-Healthcare System for Cloud-Assisted Body Area Networks, arXiv:.org, Cornell University Library, Feb. 11, 2017 (9 pages).

* cited by examiner

- K ← GenKey($1^\lambda$): Let $\mathcal{F}_1 : \{0,1\}^\lambda \times \{0,1\}^* \to \{0,1\}^\lambda, \mathcal{F}_3 : \{0,1\}^\lambda \times \{0,1\}^* \to \{0,1\}^{3\lambda}$ be two pseudorandom functions, $\mathcal{H} : \{0,1\}^* \to \{0,1\}^{2\lambda}$ be a secure hash function, SE be a secure symmetric key encryption, Mac be a secure message authentication code. Given the security parameter $\lambda$, the data owner selects $\mathcal{K} \leftarrow \{0,1\}^\lambda$, runs SE.GenKey to get $\mathcal{K}_{SE}$, runs Mac.GenKey to get $\mathcal{K}_{Mac}$, and sets K = $(\mathcal{K}, \mathcal{K}_{SE}, \mathcal{K}_{Mac})$.

- $((\text{state}'_c), (\text{state}'_s, C)) \leftarrow$ AddFile$((K, \text{state}_c, f), (\text{state}_s))$ : Suppose that the identifier of file $f$ is ID$(f)$ and the set of keywords extracted from $f$ is $W(f) = \{w_1, \ldots, w_l\}$. Note that when the system was initialized, state$_c$ = (TBL$_c = \emptyset$, BF$_c = \emptyset$) and state$_s$ = (TBL$_s = \emptyset$, BF$_s = \emptyset$) where TBL$_c$ and TBL$_s$ are two hash tables, and BF$_c$ and BF$_s$ are two bloom filters. The protocol proceeds as follows:

The data owner:

Let Ind = $\emptyset$, and run $C \leftarrow$ SE.Enc$(\mathcal{K}_{SE}, f)$ for file $f$
    for *each keyword* $w \in W(f)$ do
        Let $\mathcal{K}_{prev} = 0^\lambda$, cnt$_{prev} = 0$, cnt = 1, $\gamma_{prev} = 0^\lambda$
        if $w \in$ TBL$_c$ then
            Retrieve (cnt, $\gamma_{cnt}$) from TBL$_c$ with respect to $w$
            Let $\mathcal{K}_{prev} := \mathcal{F}_1(\mathcal{K}, \mathcal{H}(w\|\text{cnt}))$, cnt$_{prev}$ = cnt, $\gamma_{prev} = \gamma_{cnt}$, and cnt = cnt + 1
        end
        Compute $\mathcal{K}_{cnt} \leftarrow \mathcal{F}_1(\mathcal{K}, \mathcal{H}(w\|\text{cnt}))$, $\gamma_{cnt} = \gamma_{prev} \oplus$ Mac.MacGen$(\mathcal{K}_{Mac}, C\|w)$ (The output of Mac.MacGen is $\lambda$-bit length)
        Compute $\tau_{cnt} = \mathcal{F}_1(\mathcal{K}, w\|\text{cnt})$, $\phi_{cnt} = (\mathcal{F}_1(\mathcal{K}, w\|\text{cnt}_{prev})\|\mathcal{K}_{prev}\|\gamma_{cnt}) \oplus \mathcal{F}_3(\mathcal{K}_{cnt}, \tau_{cnt})$
        Compute BF$_c \leftarrow$ BFAdd(BF$_c, \tau_{cnt}$)
        Let TBL$_c[w] :=$ (cnt, $\gamma_{cnt}$), Ind = Ind $\bigcup \{(\tau_{cnt}, \phi_{cnt})\}$
    end
    Generate the MAC $\sigma \leftarrow$ Mac.MacGen$(\mathcal{K}_{Mac}, \text{BF}_c\|T)$ where $T$ is the current time stamp
    Send $(C, \text{ID}(f), \text{Ind}, \sigma, T)$ to the server and let state$'_c$ = (TBL$_c$, BF$'_c$)

The server:

Upon receiving $(C, \text{ID}(f), \text{Ind}, \sigma, T)$ from the data owner, the server proceeds as follows:

for *each* $(\tau, \phi) \in$ Ind do
        Let TBL$_s[\tau] := \phi\|\text{ID}(f)$ and BF$_s \leftarrow$ BFAdd(BF$_s, \tau$)
    end
    Store $C$ locally and set state$'_s$ = (TBL$_s$, BF$_s, \sigma, T$)

Suppose the data owner generated $r \leftarrow \{0,1\}^\lambda$ and securely shared $r$ with authorized users and the server.

- token ← GenToken(K, BF$_c, r, w$): The data owner generates the search token as follows: (i) Retrieve (cnt, $\gamma_{cnt}$) from TBL$_c$ with respect to $w$; (ii) Compute $\mathcal{K}_{cnt} = \mathcal{F}_1(\mathcal{K}, \mathcal{H}(w\|\text{cnt}))$; and (iii) Let token = SE.Enc$(r, \mathcal{F}_1(\mathcal{K}, w\|\text{cnt})\|\mathcal{K}_{cnt})$, which will be sent to the server.

- (rst, prof) ← Search(state$_s, r$, token): The server runs SE.Dec$(r, \text{token})$ to get $(\mathcal{F}_1(\mathcal{K}, w\|\text{cnt})\|\mathcal{K}_{cnt}$, and conducts the search by retrieving $\phi_{cnt}\|\text{ID}(f)$ from TBL$_s$ with respect to $\tau' = \mathcal{F}_1(\mathcal{K}, w\|\text{cnt})$, computing $\phi_{cnt} \oplus \mathcal{F}_3(\mathcal{K}_{cnt}, \tau')$ to get $\gamma_{cnt}$, letting $\mathcal{K}' = \mathcal{K}_{cnt}$, prof = $(\sigma, T, \text{BF}_s, \gamma_{cnt})$, rst = $\emptyset$, and while $\mathcal{K}' \neq 0^\lambda$ do
        Retrieve $\phi\|\text{ID}(f)$ from TBL$_s$ with respect to $\tau'$, and let rst = rst $\bigcup \{\text{ID}(f)\}$
        Let $\tau'\|\mathcal{K}'\|\gamma' = \phi \oplus \mathcal{F}_3(\mathcal{K}', \tau')$ (which results in $\mathcal{F}_1(\mathcal{K}, w\|(i-1))\|\mathcal{K}_{i-1}\|\gamma_{i-1}$ if the current counter is $i$)
    end
    Return rst as the search result and prof as the proof

- SSEVerify$(\mathcal{K}, w, \text{cnt}, \text{rst}, \text{prof})$: If the size of prof is not equal to the counter cnt, then the data owner returns 0 and aborts. Otherwise the data owner verifies the correctness as follows:

○ Given ID$(f_i) \in$ rst, $1 \leq i \leq$ cnt, fetch encrypted data files $C_1, \ldots, C_{cnt}$ from the server.
    ○ If the following two equations hold, then output 1; otherwise output 0:

$$\bigoplus_{i=1}^{cnt} \text{Mac.MacGen}(\mathcal{K}_{Mac}, C_i\|w) \stackrel{?}{=} \gamma_{cnt} \qquad \text{Mac.MacGen}(\mathcal{K}_{Mac}, \text{BF}_s\|T) \stackrel{?}{=} \sigma$$

FIGURE 2

METHOD AND SYSTEM FOR DYNAMIC SEARCHABLE SYMMETRIC ENCRYPTION WITH FORWARD PRIVACY AND DELEGATED VERIFIABILITY

CROSS-REFERENCE TO RELATED APPLICATIONS

This application is a 35 U.S.C. § 371 National Stage Application of PCT/EP2017/068734 filed on Jul. 25, 2017, which claims the benefit of U.S. Provisional Application No. 62/366,320, filed Jul. 25, 2016, the disclosures of which are herein incorporated by reference in their entirety.

FIELD

This disclosure relates generally to searchable symmetric encryption and, more particularly, to a dynamic searchable symmetric encryption system and method with forward privacy and delated verifiability.

BACKGROUND

Unless otherwise indicated herein, the materials described in this section are not prior art to the claims in this application and are not admitted to the prior arty by inclusion in this section.

The integration of cloud computing and Internet of Things (IoTs) is quickly becoming the key enabler for the digital transformation of the healthcare industry by offering comprehensive improvements in patient engagements, productivity and risk mitigation. In a typical e-healthcare setting, a group of wearable and/or implantable devices such as smart watches, bracelets, or pacemakers, which forms a wireless body area network (BAN), gathers key vital signals such as heart rate, blood pressure, temperature, or pulse oxygen from patients at home periodically. These information is aggregated into a single file known as personal health information (PHI) at an IoT gateway and then is forwarded to a cloud server for storage. Third party healthcare service providers (HSPs) can monitor patients' PHI and provide timely diagnosis and reactions by submitting on-demand queries to a cloud storage. Although the increasing adoption of cloud computing and IoT services in healthcare industry help reduce IT cost and improve patient outcomes, this paradigm shift has raised security and privacy concerns such as data and security breaches that is vulnerable to malicious attacks, software bugs or accidental errors. In particular, the healthcare regulations such as the Health Insurance Portability and Accountability Act (HIPAA) and the Health Information Technology for Economic and Clinical Health Act (HITECH) explicitly require that PHI be secured even as it migrates to the cloud infrastructure.

While simply encrypting PHI before outsourcing to the cloud can ensure the regulatory compliance of a healthcare system, it makes PHI utilization such as query submitted by third party HSPs particularly challenging. Conventional searchable encryption technology which allows encrypted documents to be searched as is by augmenting them with an encrypted search index is available. One example of the searchable encryption technology is static searchable symmetric encryption (SSE) which processes static datasets on encrypted database but does not support subsequent updates or dynamic datasets. Another example of the searchable encryption technology is dynamic SSE where a large static dataset is first processed and outsourced to the cloud storage, followed by a number of infrequent update operations. However, the dynamic SSE does not support forward privacy to prevent the cloud server from inferring sensitive information such as activity pattern or diet habit related to a patient based solely on observation of the stored encrypted indices to another data user and/or HSPs.

Thus, there is a long felt need to improve the existing system and method.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

Embodiments of the disclosure related to a dynamic searchable symmetric encryption (DSSE) system and method with forward privacy and delated verifiability. The DSSE system includes an IoT gateway, a cloud network, and at least one HSP coupled to a cloud server via the cloud network. A user such as a patient is connected to the DSSE system via any number of client devices that are either portable and/or wearable. The IoT gateway aggregates periodically collected data into a single PHI file, extract keywords, build an encrypted index, and encrypt the PHI files. The encrypted index and PHI files are then transmitted to the cloud network having a cloud server for storage. For the cloud server to retrieve multiple or all file identifiers having specific keyword, a chaining scheme is provided to implicitly link tuples corresponding to the same keyword together. The cloud server then obtains all file identifiers by iterating such scheme until the key is λ-bit of zero. The cloud server maintains a bloom filter ($BF_s$) and puts each received encrypted keyword $\mathcal{F}_1(\mathcal{K}, w\|cnt)$ into the bloom filter $BF_s$. An authorized user generates a symmetric key r and is securely shared with the cloud server. All authorized users such that a search token of keyword w generated by authorized users be SE.Enc(r, $(\mathcal{F}(\mathcal{K}, w\|cnt))$, $\mathcal{K}_{cnt}$) and the cloud server can recover $(\mathcal{F}(\mathcal{K}, w\|cnt), \mathcal{K}_{cnt})$ with the stored r via SE.Dec, where SE is a secured symmetric encryption. The authorized users use the timestamp T together with the bloom filter $BF_c$ to generate the MAC. New file is periodically uploaded so that authorized users can use the timestamp T to assure the aggregate MAC is newly generated by the data owner. Authorized users may use at least one binary search to accelerate the guessing of the latest counter cnt.

BRIEF DESCRIPTION OF THE DRAWINGS

These and other features, aspects, and advantages of this disclosure will become better understood when the following detailed description of certain exemplary embodiments is read with reference to the accompanying drawings in which like characters represent like arts throughout the drawings, wherein:

FIG. 2 is a table illustrating a full-fledged DSSE construction for use in the DSSE architecture network of FIG. 1 in accordance with a described embodiment of the disclosure.

DETAILED DESCRIPTION

Figure 1:
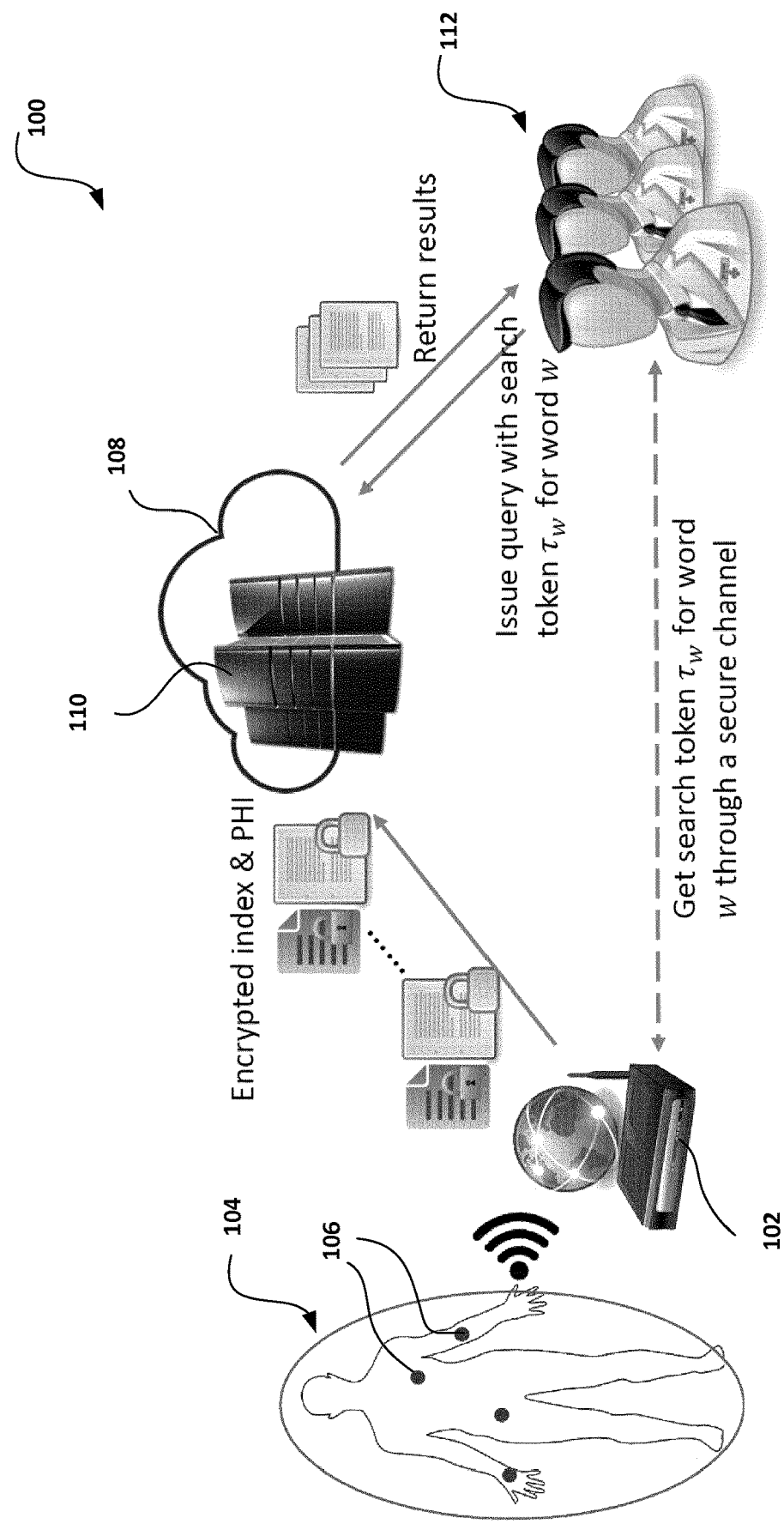
FIG. 1 is a block diagram of a dynamic searchable symmetric encryption (DSSE) architecture network in accordance with a described embodiment of the disclosure.

The following description is presented to enable any person skilled in the art to make and use the described embodiments, and is provided in the context of a particular application and its requirements. Various modifications to the described embodiments will be readily apparent to those skilled in the art, and the general principles defined herein may be applied to other embodiments and applications without departing from the spirit and scope of the described embodiments. Thus, the described embodiments are not limited to the embodiments shown, but are to be accorded the widest scope consistent with the principles and features disclosed herein.

A DSSE architecture network enables multi-user such as data owners and data users to conduct privacy-preserving search on the encrypted PHIs stored in a cloud network and verify the correctness and completeness of retrieved search results simultaneously is provided. The data owners and data users may be patients, HSPs, or combination thereof. An IoT gateway generates PHI files and transmits the PHI files to a cloud network periodically for storage thus enable the DSSE architecture network to achieve a sub-linear search efficiency and forward privacy by maintaining an increasing counter for each keyword at the IoT gateway. The cloud network therefore does not need to learn whether the newly stored PHI files contain specific keywords. Any number of HSPs such as data users provides healthcare services for the patient by searching, querying, and/or retrieving user's encrypted PHIs incrementally stored on the cloud network in a privacy and verifiable manner. In one embodiment, the patient delegated verifiability derives from a combination of a Bloom filter and aggregate message authentication code.

FIG. 1 illustrates an exemplary embodiment of a dynamic searchable symmetric encryption (DSSE) architecture network 100. The DSSE architecture network 100 includes an IoT gateway 102, a cloud network 108, and at least one HSP 112 coupled to a cloud server 110 via the cloud network 108. A user such as a patient 104 is connected to the DSSE architecture network 100 via any number of client devices that are either portable and/or wearable. Although not illustrated, the DSSE architecture network 100 can accommodate any number of client devices carried or worn by the patient 104. One or more client devices defined as BAN 106 monitor health status of the patient 104 and the client devices connected to each other may exchange and share the monitored health status. For example, the client devices may be pacemakers, wrist health monitoring systems, watches, bracelets, rings, patches, headbands, wristbands, chest bands, glasses, goggles, hearing aids, earpieces, headphones, thin or thick client devices, cellular phones, tablets, personal digital assistants, laptops, or any suitable client devices. The IoT gateway 102 is a data aggregator and is configured to aggregate periodically collected data into a single PHI file, extract keywords, build an encrypted index, and encrypt the PHI files. Although one IoT gateway 102 is illustrated, more than one IoT gateway 102 may be connected and integrated into the DSSE architecture network 100. The encrypted index and PHI files are then transmitted to the cloud network 108 for storage. The cloud server 110, in some embodiments, can represent one or more servers, one or more data stores, and so on. In alternate embodiments, the cloud server 110 can be distributed over plural cloud networks 108 using any protocol or combination of protocols. As an example, the cloud server 110 can represent a cloud storage that provide storage resources at one or more locations. The user 104 can interact with the cloud storage using the client devices of BAN 106 via the IoT gateway 012. In one embodiment, the encrypted index and the PHI files created by the IoT gateway 102 is stored in the cloud network 108 periodically for example every 10 minutes. In some embodiments, the PHI files may be stored in the cloud network 108 periodically in any predetermined threshold. Since the PHI files are always transmitted and added/stored into the cloud storage over the cloud network 108, file deletion, file modification is eliminated. Multiple HSPs 112 may be data users and provide healthcare services for the patient 104 by searching, querying, and/or retrieving user's encrypted PHIs incrementally stored on the cloud network 108 in a privacy and verifiable manner. One or more HSPs 112 may obtain search token $\tau_w$ for word $w$ from the IoT gateway 102 through a secure channel.

The data owner or the patient 104 associates to each keyword and counter, indicating the number of outsourced encrypted files having the keyword. That is, the data owner or the patient 104 locally maintains the state information, i.e. pairs of keyword and the counter. Suppose the counter associated to keyword w is cnt, the index with respect to w, stored in the cloud server 110 of the cloud network 108 is:

$$\tau_1 = \mathcal{F}_1(\mathcal{K}, w\|1), ID(f_1)$$
$$\tau_2 = \mathcal{F}_1(\mathcal{K}, w\|2), ID(f_2)$$
$$...$$
$$\tau_{cnt-1} = \mathcal{F}_1(\mathcal{K}, w\|cnt-1), ID(f_{cnt-1})$$
$$\tau_{cnt} = \mathcal{F}_1(\mathcal{K}, w\|cnt), ID(f_{cnt})$$

Where F1 is a secure pseudorandom function, K is a private key and $f1 \ldots, f_{cnt}$ are files having keyword w.

When adding a new file $f$ containing the keyword w, the data owner or the patient 104 generates $$\tau_{cnt+1} = \mathcal{F}_1(\mathcal{K}, w\|cnt+1), ID(f)$$

which is sent to the cloud server 110 of the cloud network 108, thus, the cloud server 110 does not know whether $T_{cnt+1}$ is generated from the keyword w the same as that of $T_i$, $1 \le i \le cnt$. The data owner or the patient 104 does not need to maintain all previous states for each keyword w locally in order to achieve forward privacy because there is no file deletion for streaming data.

For the cloud server 110 to retrieve multiple or all file identifiers having specific keyword, a chaining scheme is provided to implicitly link tuples corresponding to the same keyword together, assuming $\tau_0 = \mathcal{F}_1(\mathcal{K}, w\|0)$):

$$\tau_1 = \mathcal{F}_1(\mathcal{K}, w\|1), \langle \tau_0\|0^\lambda \rangle \oplus \mathcal{F}_2(\mathcal{K}_1, \tau_1), ID(f_1)$$
$$\tau_2 = \mathcal{F}_1(\mathcal{K}, w\|2), \langle \tau_1\|\mathcal{K}_1 \rangle \oplus \mathcal{F}_2(\mathcal{K}_2, \tau_2), ID(f_2)$$
$$...$$
$$\tau_{cnt-1} = \mathcal{F}_1(\mathcal{K}, w\|(cnt-1)),$$
$$\langle \tau_{cnt-2}\|\mathcal{K}_{cnt-2} \rangle \oplus \mathcal{F}_2(\mathcal{K}_{cnt-1}, \tau_{cnt-1}), ID(f_{cnt-1})$$
$$\tau_{cnt} = \mathcal{F}_1(\mathcal{K}, w\|cnt), \langle \tau_{cnt-1}\|\mathcal{K}_{cnt-1} \rangle \oplus \mathcal{F}_2(\mathcal{K}_{cnt}, \tau_{cnt}), ID(f_{cnt})$$

where $F_2$ is another secure pseudorandom function and $K_i$, $1 \le i \le cnt$ is a random key derived from the counter i. Without knowing $K_i$, $i \ge cnt$, the server cannot link $T_{cnt}$ with $T_j$, $j < cnt$, even though $K_i$ and $T_{cnt}$ may be generated from the same keyword but different counter cnt. On the other hand, given $T_{cnt}$ and $K_{cnt}$, the cloud server 110 is able to obtain $ID(f_{cnt})$ and recover $T_{cnt-1}$ and $T_{cnt-1}$ by computing:

$$\langle \tau_{cnt-1} \| \mathcal{K}_{cnt-1} \rangle \oplus \mathcal{F}_2(\mathcal{K}_{cnt}, \tau_{cnt}) \oplus \mathcal{F}_2(\mathcal{K}_{cnt}, \tau_{cnt})$$

The cloud server 100 then obtains all file identifiers by iterating such process until the key is λ-bit of zero.

FIG. 2 illustrates a full-fledged DSSE construction 200 for use in the DSSE architecture network of FIG. 1. A document-and-guess approach is implemented wherein the cloud server 110 maintains a bloom filter ($BF_s$) and puts each received encrypted keyword $\mathcal{F}_1(\mathcal{K}, w\|cnt)$ into the bloom filter $BF_s$. The authorized user such as HSP, having a secret key and fetching $BF_s$ from the cloud server 110, can guess the latest counter value by enumerating (1, ..., cnt, cnt+1) such that $\mathcal{F}_1(\mathcal{K}, w\|cnt)$ is an element hashed to $BF_s$. In order to allow the data owner or the patient 104 using any suitable client devices or BANs 106 to revoke authorized user's search capability, a group key approach is implemented wherein the data owner or the patient 104 generates a symmetric key r and is securely shared with the cloud server 110. All authorized users, e.g. HSP, such that a search token of keyword w generated by authorized users be SE.Enc(r, ($\mathcal{F}(\mathcal{K}, w\|cnt)$, $\mathcal{K}_{cnt}$) and the cloud server 110 can recover ($\mathcal{F}(\mathcal{K}, w\|cnt)$, $\mathcal{K}_{cnt}$) with the stored r via SE.Dec, where SE is a secured symmetric encryption. When an authorized data user is revoked, the data owner using any suitable client devices or BANs 106 only needs to update the group key r to r' and the revoked user cannot generate valid search token without knowing r'.

In the data owner side, each entry of the hash table $TBL_c$ includes (w, cnt, $\gamma_{cnt}$), where $\gamma_{cnt}$ is the aggregation of the MAC for the concatenation of the file and w. Concatenating the file and w as input prevents the replacement attack, i.e. given keyword $w_1$, the cloud server 110 may return the aggregate MAC and the set of file identifiers, which is the search result of $w_2$ if both keywords have the same number of returning file identifiers. Also, the data owner using any suitable client devices or BANs 106 uses the timestamp T together with the bloom filter $BF_c$ to generate the MAC to further prevent the replaying attack that the cloud server may return stale search result. New file is periodically uploaded for example every ten minutes or any suitable threshold so that authorized users can use the timestamp T to assure the aggregate MAC is newly generated by the data owner. Authorized users may use at least one binary search to accelerate the guessing of the latest counter cnt. In one embodiment, the authorized user sets a large enough upper bound Max and conducts a binary search for the latest counter cnt with [1, Max} such that $\mathcal{F}_1(\mathcal{K}, w\|cnt)$ is an element hashed to $BF_s$ while $\mathcal{F}_1(\mathcal{K}, w\|cnt+1)$ is not. The number of elements hashed into $BF_s$ then become very huge; when generating $\mathcal{F}_1(\mathcal{K}, w\|cnt)$ for keyword w, the counter value cnt is always increasing. To keep low false positive rate, a regular update scheme is implemented. Given the state information $TBL_c$, the data owner using any suitable client devices or BANs 106 regularly generates a new bloom filter $BF_c$ which implicitly stores the current counter $cnt_L$ for each keyword w, generates the MAC and sends $BF_c$ and the MAC to the cloud server. In one embodiment, the data owner using any suitable client devices or BANs 106 hashes $\mathcal{F}_1(\mathcal{K}, w\|pos\|digit_{pos})$ to $BF_c$ where $digit_{pos}$ is the latest significant digit of $cnt_L$ where pos=1, and the authorized user can guess $cnt_L$ by enumerating the combination of pos=1, ... and $digit_{pos}$=0, ... 9. The cloud server lets $BF_s$=$BF_c$. After receiving $BF_s$, the authorized user extracts the counter $cnt_L$ and then guesses the latest counter starting from $cnt_L$. In doing so, $BF_s$ only contains elements with counters beginning from $cnt_L$ rather than from 1 from the keyword w, and therefore its size can be reduced while either keeping the same false positive rate or keeping the false positive rate low.

The embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling with the sprit and scope of this disclosure.

Embodiments within the scope of the disclosure may also include non-transitory computer-readable storage media or machine-readable medium for carrying or having computer-executable instructions or data structures stored thereon. Such non-transitory computer-readable storage media or machine-readable medium may be any available media that can be accessed by a general purpose or special purpose computer. By way of example, and not limitation, such non-transitory computer-readable storage media or machine-readable medium can comprise RAM, ROM, EEPROM, CD-ROM or other optical disk storage, magnetic disk storage or other magnetic storage devices, or any other medium which can be used to carry or store desired program code means in the form of computer-executable instructions or data structures. Combinations of the above should also be included within the scope of the non-transitory computer-readable storage media or machine-readable medium.

Embodiments may also be practiced in distributed computing environments where tasks are performed by local and remote processing devices that are linked (either by hardwired links, wireless links, or by a combination thereof) through a communications network.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

While the patent has been described with reference to various embodiments, it will be understood that these embodiments are illustrative and that the scope of the disclosure is not limited to them. Many variations, modifications, additions, and improvements are possible. More generally, embodiments in accordance with the patent have been described in the context or particular embodiments. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A dynamic searchable symmetric encryption (DSSE) system comprising:
    a body area network (BAN) configured to generate a first symmetric key;
    a health service provider (HSP) configured to generate a first search token of a keyword using a second symmetric key after the HSP is revoked;
    a cloud server configured to maintain a bloom filter; and
    a cloud network communicatively coupled to the HSP and to the BAN;
    wherein the BAN is further configured to update the first symmetric key to the second symmetric key after the HSP is revoked,
    wherein the cloud network is configured (i) to recover the first search token using the second symmetric key, and (i) to recover a second search token using the first symmetric key before the HSP is revoked,
    wherein the second search token is different from the first search token, and
    wherein the BAN is further configured to generate a message authentication code using a timestamp and the bloom filter.

2. The DSSE system of claim 1 further comprising:
    a gateway configured (i) to periodically collect data from at least one of the HSP and the BAN, and (ii) to aggregate the collected data in a single personal health information (PHI) file.

3. The DSSE system of claim 2 wherein the gateway is further configured (i) to extract keywords from the PHI file, (ii) to build an encrypted index into the PHI file, and (iii) to encrypt the PHI file.

4. The DSSE system of claim 3 wherein the gateway is further configured to transmit the PHI file, including the encrypted index, to the cloud server for storage.

5. The DSSE system of claim 4 wherein the cloud server is within the cloud network.

6. The DSSE system of claim 5 wherein the HSP is further configured to retrieve the bloom filter from the cloud server using a secret key.

7. The DSSE system of claim 2, wherein the BAN is a pacemaker, a wrist mounted health monitoring device, a watch, a bracelet, a ring, a patch, a headband, a wristband, a chest band, glasses, goggles, a hearing aid, an earpiece, or headphones.

* * * * *